(12) United States Patent
Jamison et al.

(10) Patent No.: US 11,761,274 B2
(45) Date of Patent: Sep. 19, 2023

(54) TEST APPARATUS FOR MEASURING PARTICLE PLUGGING OF A SIMULATED FRACTURE

(71) Applicant: Halliburton Energy Services, Inc., Houston, TX (US)

(72) Inventors: Dale E. Jamison, Humble, TX (US); Andrew Vos, Spring, TX (US); James R. Jones, Richmond, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 17/555,001

(22) Filed: Dec. 17, 2021

(65) Prior Publication Data
US 2023/0193704 A1    Jun. 22, 2023

(51) Int. Cl.
| | |
|---|---|
| *G01N 33/28* | (2006.01) |
| *F04B 15/02* | (2006.01) |
| *F04B 23/04* | (2006.01) |
| *G01N 11/04* | (2006.01) |
| *E21B 21/00* | (2006.01) |
| *G01N 15/02* | (2006.01) |
| *G01N 21/01* | (2006.01) |

(Continued)

(52) U.S. Cl.
CPC ............ *E21B 21/003* (2013.01); *F04B 15/02* (2013.01); *F04B 23/04* (2013.01); *F04B 23/06* (2013.01); *F04B 49/06* (2013.01); *G01N 15/02* (2013.01); *G01N 15/0205* (2013.01); *G01N 21/01* (2013.01); *G01N 21/90* (2013.01); *G01N 33/2823* (2013.01); *F04B 2205/01* (2013.01); *F04B 2205/04* (2013.01); *G01N 11/04* (2013.01); *G01N 2021/0106* (2013.01)

(58) Field of Classification Search
CPC .. E21B 21/003; G01N 15/02; G01N 15/0205; G01N 21/01; G01N 21/90; G01N 33/2823; G01N 11/04; G01N 2021/0106
See application file for complete search history.

(56) References Cited

U.S. PATENT DOCUMENTS

| | | | | |
|---|---|---|---|---|
| 4,011,747 | A * | 3/1977 | Shaw | ............... H03H 9/145 73/620 |
| 8,151,633 | B2 * | 4/2012 | Jamison | ............ G01N 33/2823 73/54.39 |

(Continued)

FOREIGN PATENT DOCUMENTS

| | | | |
|---|---|---|---|
| CN | 111982758 | A * | 11/2020 |
| CN | 112229777 | A * | 1/2021 |

(Continued)

*Primary Examiner* — Kristina M Deherrera
*Assistant Examiner* — Fatemeh Esfandiari Nia
(74) *Attorney, Agent, or Firm* — Kilpatrick Townsend & Stockton LLP

(57) ABSTRACT

A test apparatus can measuring particle plugging of a simulated fracture. The test apparatus can include a first test component having a first surface and a second test component having a second surface. The second test component can be positionable relative to the first test component to create a simulated fracture between the first surface and the second surface. The test apparatus can include a visualization area of at least one of the first test component or the second test component can be positioned between a fluid inlet and a fluid outlet along at least a portion of the simulated fracture.

16 Claims, 5 Drawing Sheets

(51) Int. Cl.
*G01N 21/90* (2006.01)
*F04B 49/06* (2006.01)
*F04B 23/06* (2006.01)

(56) References Cited

U.S. PATENT DOCUMENTS

| | | | |
|---|---|---|---|
| 2010/0018294 A1* | 1/2010 | Tonmukayakul | G01N 11/14 73/54.39 |
| 2010/0139387 A1* | 6/2010 | Jamison | G01N 33/2823 73/152.25 |
| 2015/0292279 A1* | 10/2015 | Wang | E21B 21/003 166/293 |
| 2017/0089153 A1* | 3/2017 | Teodorescu | E21B 43/10 |
| 2021/0071408 A1* | 3/2021 | Mouawad | E04B 2/04 |
| 2021/0254450 A1* | 8/2021 | Hitchcock | G01N 33/24 |
| 2022/0213761 A1* | 7/2022 | Bulekbay | E21B 37/02 |

FOREIGN PATENT DOCUMENTS

| | | | |
|---|---|---|---|
| CN | 113551873 A | * | 10/2021 |
| EA | 030301 B1 | * | 7/2018 |

* cited by examiner

TEST APPARATUS FOR MEASURING PARTICLE PLUGGING OF A SIMULATED FRACTURE

TECHNICAL FIELD

The present disclosure relates generally to wellbore operations and, more particularly (although not necessarily exclusively), to a test apparatus for measuring particle plugging of a simulated fracture.

BACKGROUND

The hydrocarbon extraction industry makes use of wellbore drilling to explore and recover natural resources such as water, oil, and gas. During wellbore drilling, drilling fluid is pumped into the well to enable hydrocarbons to be released. The hydrocarbons, along with the drilling fluid, flow up the wellbore through a wellbore annulus to be extracted. Occasionally, drilling fluid can uncontrollably flow into a formation, reducing the amount of drilling fluid returning to the surface, meaning there is a loss of circulation. Lost circulation events are costly to drilling operations because remediation processes and nonproductive time are spent to repair the problem. Materials can be added to the drilling fluid which act to plug fractures in the wellbore and reduce or prevent the outward flow of the drilling fluid, thereby reducing or preventing lost circulation. The plugging of fractures may also strengthen the wellbore.

DETAILED DESCRIPTION

Figure 1:
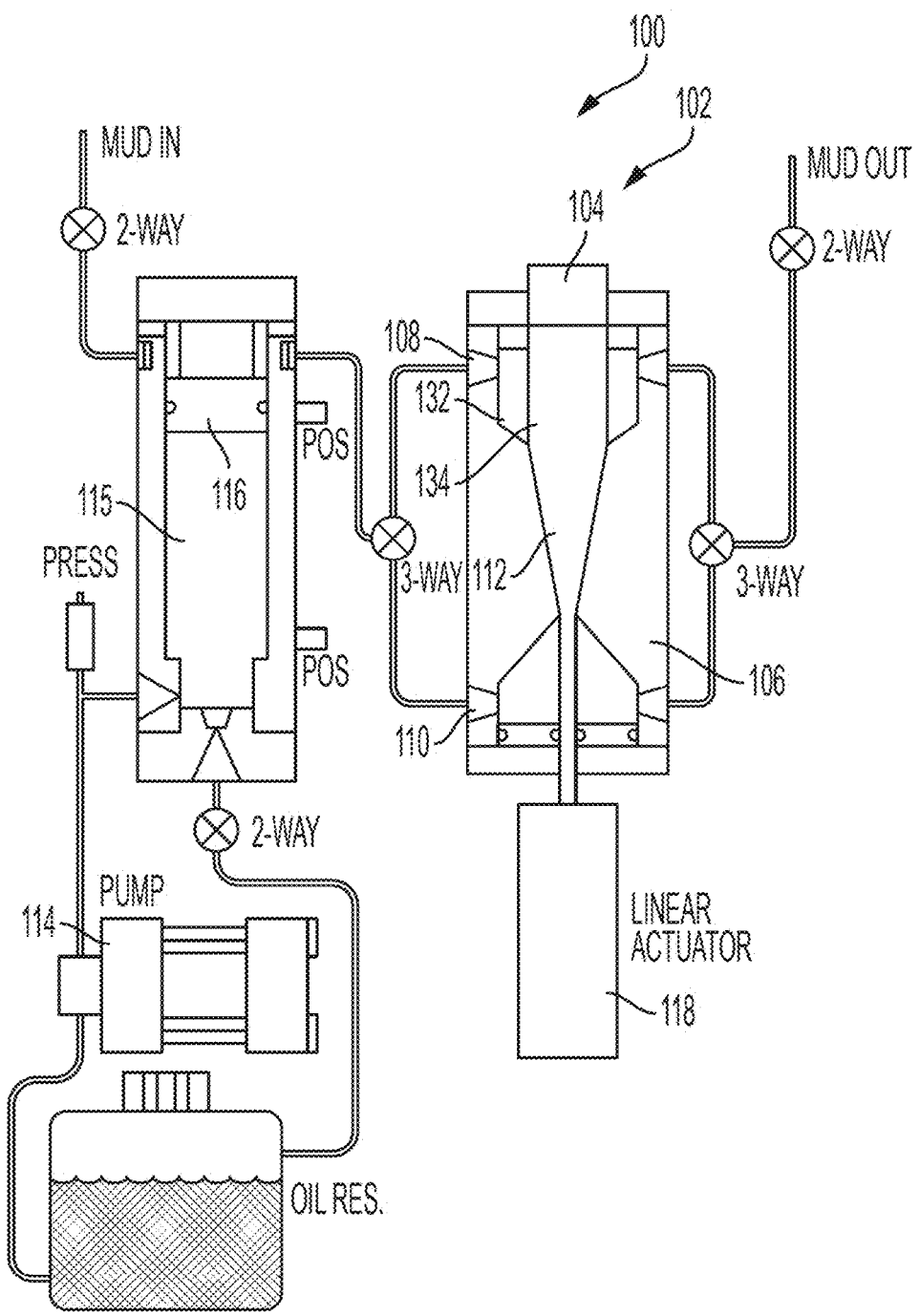
FIG. 1 is a schematic of a system for measuring particle plugging of a simulated fracture according to one example of the present disclosure.

Certain aspects and examples of the present disclosure relate to measuring particle plugging of a test fluid using a test apparatus. Particle plugging involves particles in the test fluid flowing into a simulated fracture. The test fluid can be similar to a drilling fluid that is to be used in a drilling operation and the simulated fracture can have similar properties, such as length and width, as a fracture in a wellbore. So, measuring the particle plugging can provide an indication of how fractures in a wellbore may be plugged by the drilling fluid during a drilling operation or a wellbore-strengthening operation. A determination can also be made for an adjustment to the test fluid based on the indicated particle plugging. As a result, the drilling fluid can include desirable properties for plugging fractures prior to the drilling operation, thereby reducing lost circulation, and improving a strength of the wellbore.

In some examples, a system is provided that includes a test apparatus with a simulated fracture for measuring particle plugging by a test fluid. The test apparatus can provide information of how completely particles are plugging a simulated fracture, which can help fluid engineers design background treatments for wellbore strengthening and lost circulation applications. As an example, the test apparatus may include a first test component, such as a conical cylinder, and a second test component, such as a conical plug. The conical plug can be inserted into a conical cylinder. An axial position of the conical plug may be adjusted to set a fracture width at an opening of the simulated fracture. The fracture width from the opening to a bottom of the simulated fracture may be constant or may converge to simulate a fracture. The first test component and the second test component can be manufactured so that an angle at which the fracture width converges can be predefined. A simulated fracture that converges can be referred to as a tapered-width fracture.

The conical cylinder can have a visualization area to allow optical inspection of the particles that can plug the simulated fracture. The visualization area may allow inspection by a camera or ultrasonic device. A laser may be included to provide a unique and illuminating light source to enhance how the particles are interacting with other particles to form a plug. The camera or laser may be scanned along the visualization area to enhance the image. The test apparatus may include backlighting behind the visualization area to view light transmission through the simulated fracture. In some examples, the resulting image may be analyzed by a computing device to determine a position of the various plugging particles. The position may indicate the largest size possibility for the particle.

Another configuration of the test apparatus may include two flat opposing surfaces that are used to create the simulated fracture that the test fluid may plug. One of the surfaces may be actuated relative to the other surface to set the width of the simulated fracture. The flat surfaces may be advantageous because the visualization area may have flat surfaces that will not distort perceived particle plugging characteristics. The lack of distortion can improve the ease of image processing as well as better simulate an assumed relative planar geometry of actual borehole fractures.

The image or data provided by the camera or ultrasonic device can be used to determine an adjustment for the test fluid. A desirable plugging result may include the particles being substantially evenly distributed through the simulated fracture. So, particles concentrated at the opening and at the bottom of the simulated fracture can indicate that particles in a midsize range should be added to the test fluid. Additionally, particles concentrating at the bottom of the simulated fracture can indicate that larger particle should be added to the test fluid, and particles concentrating at the opening of the simulated fracture can indicate that smaller particles should be added to the test fluid. Other parameters, such as a rate filling the simulated fracture and a volume of fluid involved in plugging the simulated fracture, may also be used to determine the adjustment for the test fluid.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions} are used to describe the illustrative aspects, but, like the illustrative aspects, should not be used to limit the present disclosure.

FIG. 1 is a schematic of a system 100 for measuring particle plugging of a simulated fracture 112 according to one example of the present disclosure. The system 100 includes a test apparatus 102 that can receive a test fluid. For example, a pump 114 can displace a piston 116 in a vessel 115 filled with the test fluid. The pump 114 may be an air-over-oil pump, or any other suitable pump. The pump 114 can provide a desired pressure to the test apparatus 102. The desired pressure may be a pressure similar to a pressure downhole in a wellbore. The system 100 may additionally include a heater to provide a desired temperature to the test apparatus 102, such as a temperature similar to a temperature downhole in a wellbore.

The test apparatus 102 can also include a first test component 106 and a second test component 104. The second test component 104 can be positioned with respect to the first test component 106 to create the simulated fracture 112. For example, the second test component 104 can be inserted within the first test component 106, and the simulated fracture 112 can be formed between an inner surface 132 of the first test component 106 and an outer surface 134 of the second test component 104. The inner surface 132 and the outer surface 134 may be at a same angle so that the simulated fracture 112 has a same width along its entire length. Alternatively, the inner surface 132 and the outer surface 134 may be at different angles so that the simulated fracture 112 is a tapered-width fracture that converges.

In an example, the system 100 can include an actuator 118, such as a linear actuator, coupled to the second test component 104 for positioning the second test component 104 with respect to the first test component 106. By using the actuator 118, the simulated fracture 112 can be set to have a desired width or length. The desired width or length can be the same as a known fracture in a wellbore.

The test apparatus 102 can receive the test fluid from the vessel 115 through a fluid inlet 108 at a top of the first test component 106. The test fluid can flow into the second test component 104. At least a portion of the test fluid can flow into the simulated fracture 112. The test fluid can include particles that can plug the simulated fracture 112. Examples of the particles include calcium carbonate, graphitic carbon, sugar cane fibers, walnut shells, and pecan shells of various sizes. Depending on the size of the particles, the particles may be able to partially or fully fill the simulated fracture 112. After flowing through the second test component 104, the test fluid can flow out of a fluid outlet 110 at a bottom of the first test component 106. The simulated fracture 112 can then be inspected, as described further in FIGS. 2-4, to determine how well the particles plugged the simulated fracture 112. The test fluid may be adjusted, such as by changing the particles in the test fluid, based on the inspection.

Figure 2:
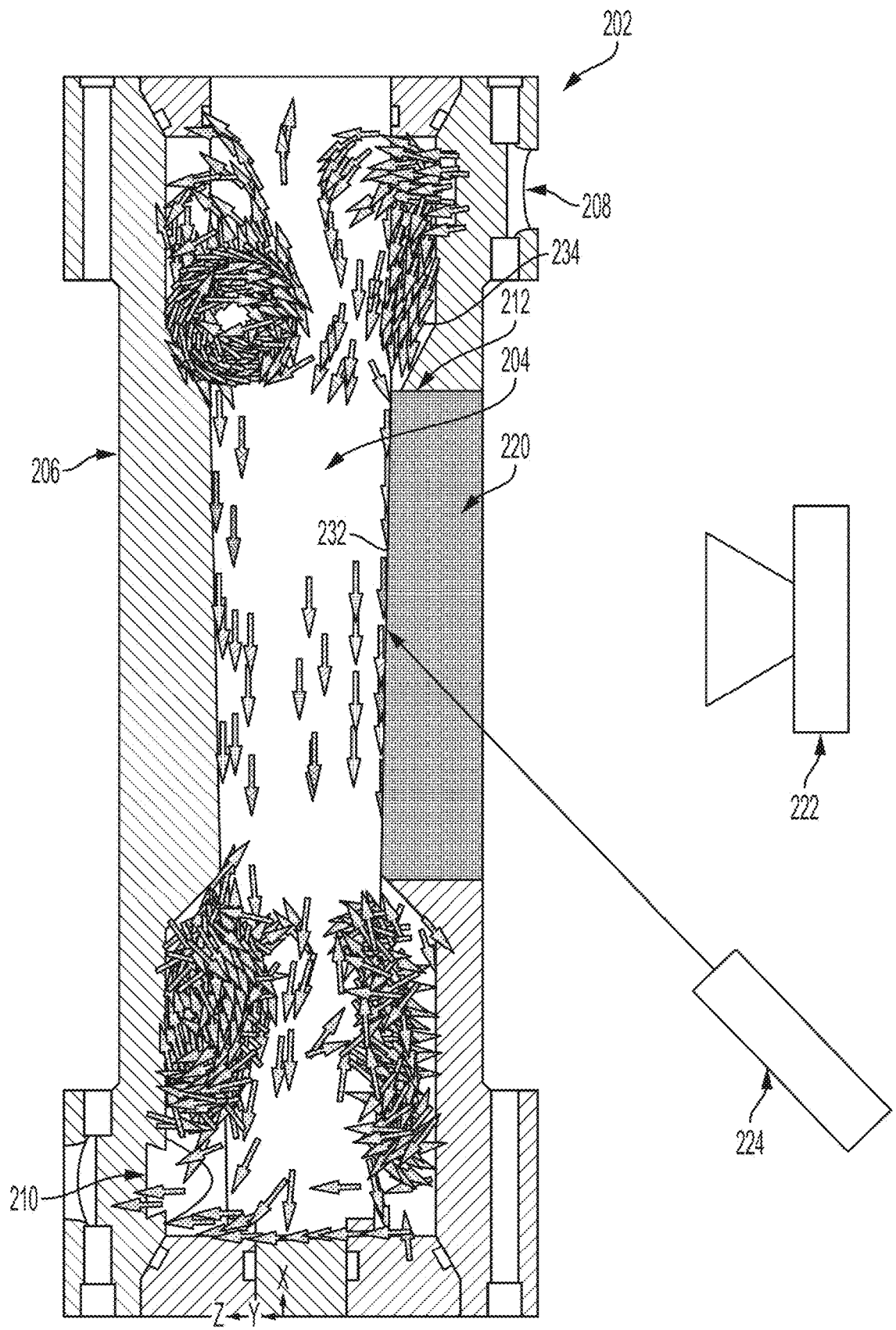
FIG. 2 is a cross-section of an example of a conical-shaped test apparatus for measuring particle plugging of a simulated fracture according to one example of the present disclosure.

FIG. 2 is a cross-section of an example of a conical-shaped test apparatus 202 for measuring particle plugging of a simulated fracture 212 according to one example of the present disclosure. The test apparatus 202 is an example of the test apparatus 102 in FIG. 1. The test apparatus 202 includes a first test component 206 that is a conical cylinder and a second test component 204 that is a conical plug. The conical plug can be inserted into the conical cylinder to create the simulated fracture 212 between an inner surface 234 of the first test component 206 and an outer surface 232 of the second test component 204. The inner surface 234 and the outer surface 232 can both be conical surfaces. The second test component 204 may be coupled to an actuator for positioning the second test component 204 relative to the first test component 206, and thereby providing the simulated fracture 212 with a particular width and length.

The test apparatus 202 can receive a test fluid, illustrated by the arrows, through a fluid inlet 208 at a top of the first test component 206. The test fluid can flow into the second test component 204. At least a portion of the test fluid can flow into the simulated fracture 212. The test fluid can include particles that can plug the simulated fracture 212. Examples of the particles include calcium carbonate, graphitic carbon, sugar cane fibers, walnut shells, and pecan shells of various sizes. Depending on the size of the particles, the particles may be able to partially or fully plug the simulated fracture 212. After flowing through the second test component 204, the test fluid can flow out of a fluid outlet 210 at a bottom of the first test component 206.

After the test fluid flows from the fluid inlet 208 to the fluid outlet 210, the simulated fracture 212 can be inspected to determine how well the particles plugged the simulated fracture 212. The first test component 206 can include a visualization area 220 positioned between the fluid inlet 208 and the fluid outlet 210 along at least a portion of the simulated fracture 212. The visualization area 220 may be a sapphire or glass plate through which the simulated fracture 212 can be visualized. Data can be generated through the visualization area 220 that is indicative of the plugging of the simulated fracture 212. For example, a camera 222 may be used to capture an image of the simulated fracture 212. The image can be sent to a computing device where the image may be either automatically or manually analyzed. Based on a distribution of the particles in the simulated fracture 212, a determination about how to adjust the test fluid can be made. It may be desirable for the particles to be evenly distributed through the simulated fracture 212. So, particles concentrating at an opening and a bottom of the simulated fracture 212 may indicate that particles in a midsize range should be added to the test fluid. The midsize range may be calculated as $$\frac{\text{opening fracture width} - \text{bottom fracture width}}{2 + \text{bottom fracture width}}.$$

Alternatively, particles concentrating at the bottom of the simulated fracture 212 can indicate that the test fluid should be adjusted to include larger particles than are currently included in the test fluid. As another example, particles concentrating at the opening of the simulated fracture 212 can indicate that the test fluid should be adjusted to include smaller particles than are currently included in the test fluid. Other parameters, such as a rate filling the simulated fracture and a volume of fluid involved in plugging the simulated fracture, may also be used to determine the adjustment for the test fluid.

In an example, a laser 224 may be used in addition with camera 222 to generate the image. The laser 224 can provide a unique and illuminating light source to enhance the particles in the simulated fracture 212 and show the particles are interacting with other particles to form a plug. The laser 224 may be scanned along the visualization area 220 to enhance the image. In some instances, the laser 224 may scan the visualization area 220 at different rates than the camera 222.

Figure 3:
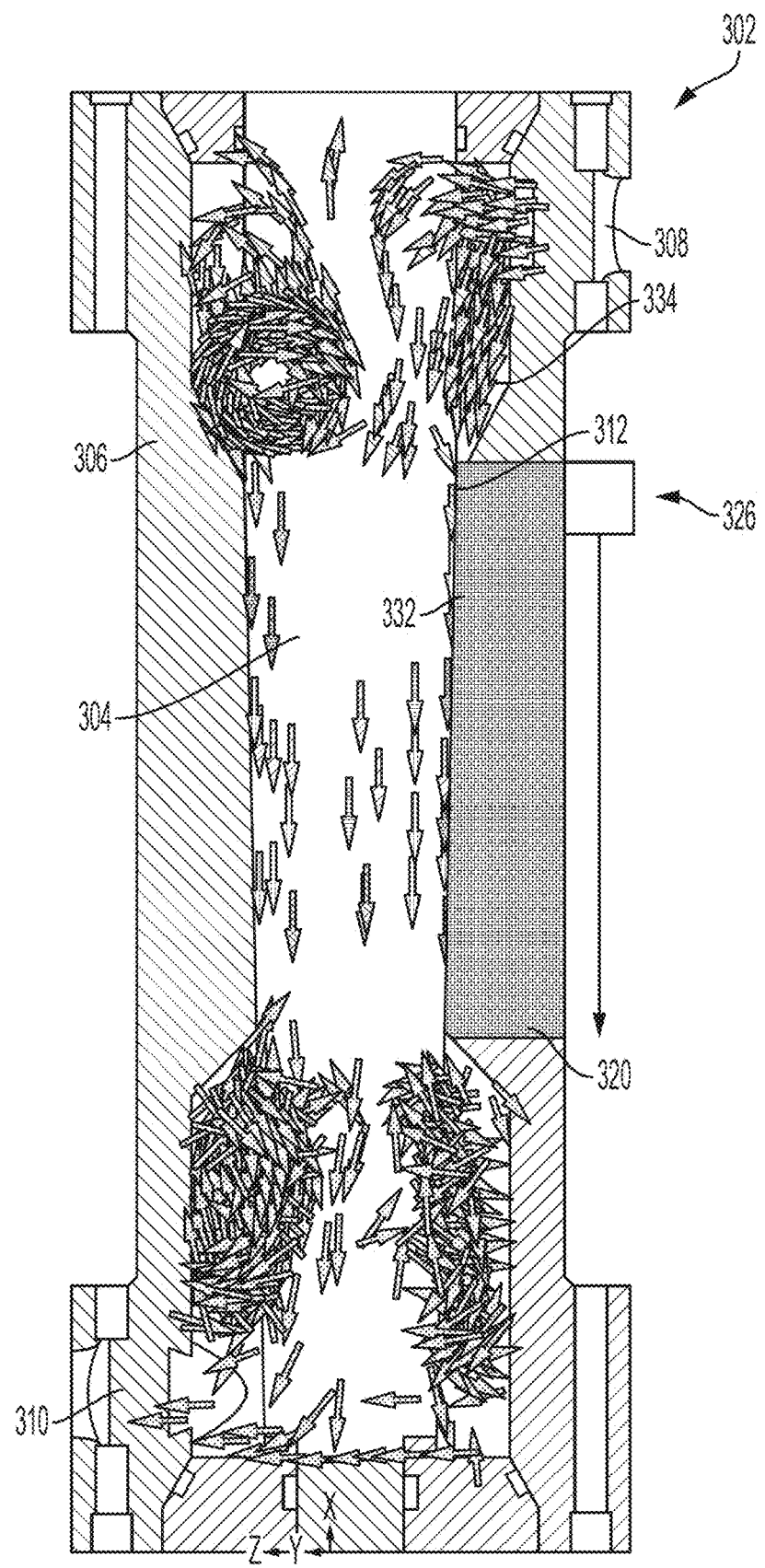
FIG. 3 is a cross-section of another example of a conical-shaped test apparatus for measuring particle plugging of a simulated fracture according to one example of the present disclosure.

FIG. 3 is a cross-section of another example of a conical-shaped test apparatus 302 for measuring particle plugging of a simulated fracture according to one example of the present disclosure. The test apparatus 302 is an example of the test apparatus 102 in FIG. 1. The test apparatus 302 includes a first test component 306 that is a conical cylinder and a second test component 304 that is a conical plug. The conical plug can be inserted into the conical cylinder to create the simulated fracture 312 between an inner surface 334 of the first test component 306 and an outer surface 332 of the second test component 304. The inner surface 334 and the outer surface 332 can both be conical surfaces. The second test component 304 may be coupled to an actuator for positioning the second test component 304 with respect to the first test component 306, and thereby providing the simulated fracture 312 with a particular width and length.

The test apparatus 302 can receive a test fluid, illustrated by the arrows, through a fluid inlet 308 at a top of the first test component 306. The test fluid can flow into the second test component 304. At least a portion of the test fluid can flow into the simulated fracture 312. The test fluid can include particles that can plug the simulated fracture 312. Examples of the particles include calcium carbonate, graphitic carbon, sugar cane fibers, walnut shells, and pecan shells of various sizes. Depending on the size of the particles, the particles may be able to partially or fully plug the simulated fracture 312. After flowing through the second test component 304, the test fluid can flow out of a fluid outlet 310 at a bottom of the first test component 306.

Subsequent to the test fluid flowing from the fluid inlet 308 to the fluid outlet 310, the simulated fracture 312 can be inspected to determine how well the particles plugged the simulated fracture 312. The first test component 306 can include a visualization area 320 positioned between the fluid inlet 308 and the fluid outlet 310 along at least a portion of the simulated fracture 312. The visualization area 320 may be a sapphire or glass plate through which the simulated fracture 312 can be visualized. Data can be generated through the visualization area 320 that is indicative of the plugging of the simulated fracture 312. For example, an ultrasonic device 326 may be used to generate the data indicating a distribution of the particles in the simulated fracture 312. The data can be sent to a computing device, where the data may be either automatically or manually analyzed. Based on a distribution of the particles in the simulated fracture 312, a determination about how to adjust the test fluid can be made, as it may be desirable for the particles to be evenly distributed through the simulated fracture 312.

Figure 4:
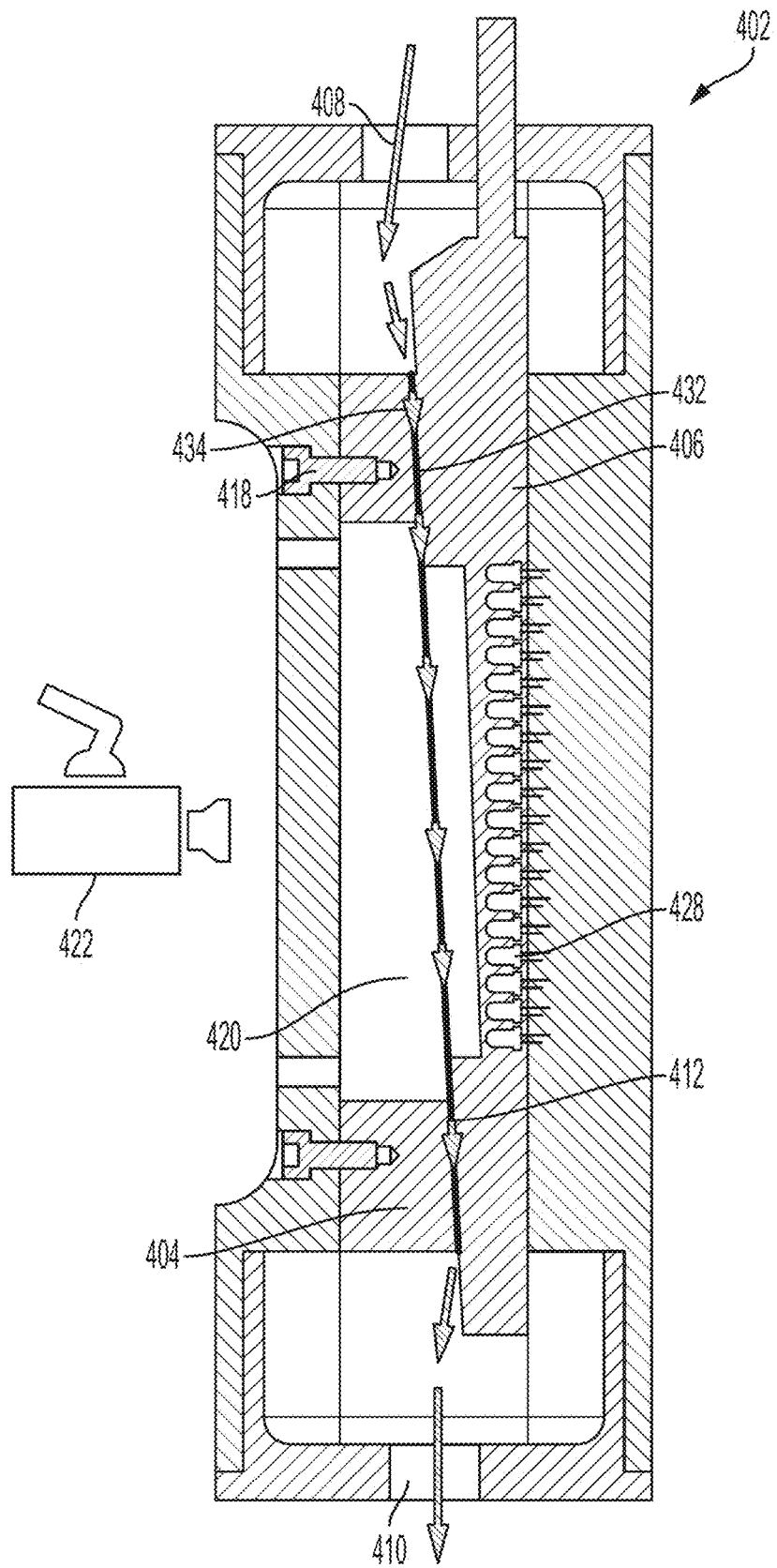
FIG. 4 is a cross-section of an example of a flat-surfaced test apparatus for measuring particle plugging of a simulated fracture according to one example of the present disclosure.

FIG. 4 is a cross-section of an example of a flat-surfaced test apparatus 402 for measuring particle plugging of a simulated fracture 412 according to one example of the present disclosure. The test apparatus 402 is an example of the test apparatus 102 in FIG. 1. The test apparatus 402 includes a first test component 406 and a second test component 404. The first test component 406 includes a first flat surface 432 that faces towards a second flat surface 434 of the second test component 404. The second test component 404 can be moved relative to the first test component 406 to create the simulated fracture 412 between the first flat surface 432 and the second flat surface 434. The second test component 404 may be coupled to an actuator 418, such as a cam, for positioning the second test component 404 with respect to the first test component 406, and thereby providing the simulated fracture 412 with a particular width and length. The first flat surface 432 and the second flat surface 434 may better simulate a relative planar geometry of borehole fractures in a wellbore compared to conical surfaces.

The test apparatus 402 can receive a test fluid, illustrated by the arrows, through a fluid inlet 408 at a top of the test apparatus 402. At least a portion of the test fluid can flow into the simulated fracture 412. The test fluid can include particles that can plug the simulated fracture 412. Examples of the particles include calcium carbonate, graphitic carbon, sugar cane fibers, walnut shells, and pecan shells of various sizes. Depending on the size of the particles, the particles may be able to partially or fully plug the simulated fracture 412. The test fluid can exit the test apparatus 402 through of a fluid outlet 410 at a bottom of the test apparatus 402.

Subsequent to the test fluid flowing from the fluid inlet 408 to the fluid outlet 410, the simulated fracture 412 can be inspected to determine how well the particles plugged the simulated fracture 412. The first test component 406 can include a visualization area 420 positioned between the fluid inlet 408 and the fluid outlet 410 along at least a portion of the simulated fracture 412. The visualization area 420 may be a sapphire or glass plate through which the simulated fracture 412 can be visualized. In FIG. 4, both the first test component 406 and the second test component 404 include a sapphire plate that makes up the visualization area 420, but in other examples only one of the first test component 406 or the second test component 404 may include the visualization area 420.

Data can be generated through the visualization area 420 that is indicative of the plugging of the simulated fracture 412. For example, a camera 422 may be used to generate an image that indicates a distribution of the particles in the simulated fracture 412. Since surfaces of the visualization area 420 can be flat, the image may have less distortion of the perceived particle plugging characteristics. The test apparatus 402 may additionally include backlighting 428, such as light emitting diodes (LEDs), behind the visualization area 420. With the backlighting 428 off, the image can capture reflected light, and with the backlighting 428 on, the image can capture transmitted light. The backlighting 428 may involve ultraviolet, infrared, single color, or white light. The image can be sent to a computing device, where the data may be either automatically or manually analyzed. Based on a distribution of the particles in the simulated fracture 412, a determination about how to adjust the test fluid can be made, as it may be desirable for the particles to be evenly distributed through the simulated fracture 412.

Figure 5:
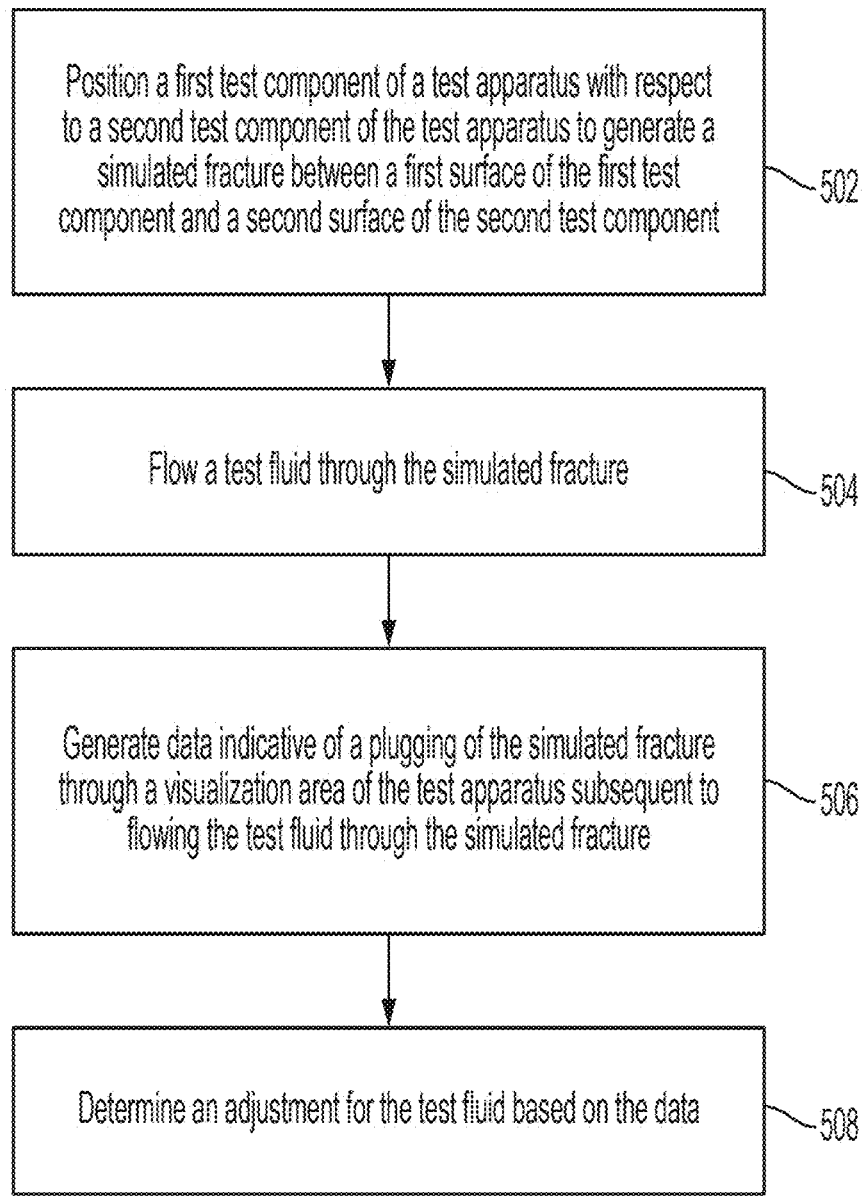
FIG. 5 is a flowchart of a process for measuring particle plugging of a simulated fracture according to one example of the present disclosure.

FIG. 5 is a flowchart of a process for measuring particle plugging of a simulated fracture according to one example of the present disclosure. At block 502, a first test component of a test apparatus is positioned with respect to a second test component of the test apparatus to generate a simulated fracture between a first surface of the first test component and a second surface of the second test component. The first test component may be a conical cylinder with a conical inner surface and the second test component may be a conical plug with a conical outer surface. Alternatively, the first test component and the second test component may have flat surfaces. An actuator coupled to the second test component can adjust the position of the first test component relative to the second test component so that a length and width of the simulated fracture can be set.

At block 504, a test fluid is flowed through the simulated fracture. The test fluid can include properties of a drilling fluid that can be flowed downhole into a wellbore for fracture plugging. For example, the test fluid can include particles, such as calcium carbonate, graphitic carbon, sugar cane fibers, walnut shells, and pecan shells, of various sizes. The test fluid can flow from a fluid inlet at a top of the test apparatus to a fluid outlet at a bottom of the test apparatus.

As the test fluid flows from the fluid inlet to the fluid outlet, at least a portion of the particles in the test fluid can enter the simulated fracture.

At block 506, data can be generated that indicates a plugging of the simulated fracture. The data can be generated through a visualization area of the test apparatus subsequent to flowing the test fluid through the simulated fracture. Examples of the data can include an image generated by a camera scanning the simulated fracture through the visualization window, or data generated by an ultrasonic device scanning the visualization window. In some examples, a laser may scan the visualization window as the data is generated to further illuminate the particles.

At block 508, an adjustment for the test fluid is determined based on the data. The data may be automatically analyzed by a computing device, or the data may be manually analyzed. The data can indicate a distribution of the particles, which is associated with the plugging of the simulated fracture. Based on the distribution of the particles in the simulated fracture, it may be determined that the test fluid is to be adjusted so that the particles may be more evenly distributed through the simulated fracture. For example, particles concentrating at an opening and a bottom of the simulated fracture may indicate that particles in a midsize range should be added to the test fluid. Additionally or alternatively, particles concentrating at the bottom of the simulated fracture can indicate that the test fluid should be adjusted to include larger particles than are currently included in the test fluid, and particles concentrating at the opening of the simulated fracture can indicate that the test fluid should be adjusted to include smaller particles than are currently included in the test fluid. The adjusted test fluid may then be flowed into the test apparatus to determine whether additional adjustments are to be made to the test fluid prior to a drilling fluid having the properties of the test fluid being flowed downhole in a wellbore.

In some aspects, a system, method, and test apparatus for measuring particle plugging of a simulated fracture are provided according to one or more of the following examples:

As used below, any reference to a series of examples is to be understood as a reference to each of those examples disjunctively (e.g., "Examples 1-4" is to be understood as "Examples 1, 2, 3, or 4").

Example 1 is a system comprising: a first test component comprising a first surface; a second test component comprising a second surface, the second test component being positionable relative to the first test component to create a simulated fracture between the first surface and the second surface; and a visualization area of at least one of the first test component or the second test component positionable between a fluid inlet and a fluid outlet along at least a portion of the simulated fracture.

Example 2 is the system of example 1, wherein the first test component comprises a conical cylinder, the first surface comprises a first conical surface, the second test component comprises a conical plug insertable into the conical cylinder, and the second surface comprises a second conical surface.

Example 3 is the system of example 1, wherein the first surface comprises a first flat surface and the second surface comprises a second flat surface.

Example 4 is the system of example(s) 1-3, further comprising: an actuator coupleable to the second test component, the actuator configured to position the second test component relative to the first test component to define a width of the simulated fracture.

Example 5 is the system of example(s) 1-4, wherein the simulated fracture comprises a tapered-width facture with the first surface having a different angle than the second surface.

Example 6 is the system of examples 1-5, further comprising: a camera configured to capture an image of the simulated fracture through the visualization area subsequent to the test fluid flowing from the fluid inlet to the fluid outlet.

Example 7 is the system of examples 1-6, further comprising: a camera configured to capture an image of the simulated fracture through the visualization area subsequent to the test fluid flowing from the fluid inlet to the fluid outlet while a laser illuminates the simulated fracture.

Example 8 is the system of example(s) 1-7, further comprising: an ultrasonic device configured to scan the visualization area subsequent to the test fluid flowing from the fluid inlet to the fluid outlet to generate data indicating a plugging of the simulated fracture.

Example 9 is a method comprising: positioning a first test component of a test apparatus relative to a second test component of the test apparatus to generate a simulated fracture between a first surface of the first test component and a second surface of the second test component; flowing a test fluid through the simulated fracture; generating data indicative of a plugging of the simulated fracture through a visualization area of the test apparatus subsequent to flowing the test fluid through the simulated fracture; and determining an adjustment for the test fluid based on the data.

Example 10 is the method of example 9, wherein positioning the first test component relative to the second test component comprises adjusting an actuator coupled to the second test component.

Example 11 is the method of example 9, wherein flowing the test fluid through the simulated fracture comprises operating a pump of the test apparatus configured to displace the test fluid from a fluid vessel into a fluid inlet of the test apparatus.

Example 12 is the method of example(s) 9-11, wherein generating the data comprises capturing an image with a camera, capturing the image while scanning the visualization area with a laser, or scanning the visualization area with an ultrasonic device.

Example 13 is the method of example(s) 9-12, wherein the first test component comprises a conical cylinder, the first surface comprises a first conical surface, the second test component comprises a conical plug insertable into the conical plug, and the second surface comprises a second conical plug.

Example 14 is the method of example(s) 9-13, wherein the first surface comprises a first flat surface and the second surface comprises a second flat surface.

Example 15 is the method of example(s) 9-14, further comprising simulating downhole conditions by controlling a temperature, a pressure, or a combination thereof of the test apparatus.

Example 16 is the method of example(s) 9-15, wherein the simulated fracture comprises a tapered-width facture with the first surface having a different angle than the second surface.

Example 17 is a test apparatus comprising: a conical cylinder comprising a conical inner surface and a visualization area; a conical plug comprising a conical outer surface; an actuator coupleable to the conical plug, the actuator configured to position the conical plug relative to the conical cylinder to create a simulated fracture between the conical inner surface and the conical outer surface; and the visualization area of the conical cylinder positionable along at least a portion of the simulated fracture.

Example 18 is the test apparatus of example 17, further comprising: a fluid inlet configured to receive a test fluid at a first location of the test apparatus; a fluid outlet configured to release at least a portion of the test fluid at a second location of the test apparatus; and a pump configured to displace the test fluid from a fluid vessel into the fluid inlet.

Example 19 is the test apparatus of example 18, further comprising: a camera configured to capture an image of the simulated fracture through the visualization area subsequent to the test fluid flowing from the fluid inlet to the fluid outlet.

Example 20 is the test apparatus of example 18, wherein the simulated fracture comprises a tapered-width facture with the conical inner surface having a different angle than the conical outer surface.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system comprising:
    a first test component comprising a first surface, the first test component comprising a conical cylinder and the first surface comprising a first conical surface portion and a first flat surface portion;
    a second test component comprising a second surface, the second test component being positionable relative to the first test component to create a simulated fracture between the first surface and the second surface, the second test component comprising a conical plug insertable into the conical cylinder, and the second surface comprising a second conical surface portion and a second flat surface portion;
    a visualization area of at least one of the first test component or the second test component positionable between a fluid inlet and a fluid outlet along at least a portion of the simulated fracture, the visualization area including the first flat surface portion and the second flat surface portion;
    a laser configured to be scanned along the visualization area to enhance imaging of a distribution of a plurality of particles of a test fluid flowing through the simulated fracture; and
    a fluid vessel defining an area containing the test fluid comprising the plurality of particles, a size of the plurality of particles being based on the distribution of the plurality of particles in the simulated fracture.

2. The system of claim 1, further comprising:
    an actuator couplable to the second test component, the actuator configured to position the second test component relative to the first test component to define a width of the simulated fracture.

3. The system of claim 1, wherein the simulated fracture comprises a tapered-width fracture with the first surface having a different angle than the second surface.

4. The system of claim 1, further comprising:
    a camera configured to capture an image of the simulated fracture through the visualization area subsequent to the test fluid flowing from the fluid inlet to the fluid outlet.

5. The system of claim 1, further comprising:
    a camera configured to capture an image of the simulated fracture through the visualization area subsequent to the test fluid flowing from the fluid inlet to the fluid outlet while the laser illuminates the simulated fracture.

6. The system of claim 1, further comprising:
    an ultrasonic device configured to scan the visualization area subsequent to the test fluid flowing from the fluid inlet to the fluid outlet to generate data indicating a plugging of the simulated fracture.

7. A method comprising:
    positioning a first test component of a test apparatus relative to a second test component of the test apparatus to generate a simulated fracture between a first surface of the first test component and a second surface of the second test component, the first test component comprising a conical cylinder, the first surface comprising a first conical surface portion, the second test component comprising a conical plug insertable into the conical cylinder, and the second surface comprising a second conical surface portion, wherein the first surface further comprises a first flat surface portion and the second surface further comprises a second flat surface portion;
    flowing a test fluid comprising a plurality of particles through the simulated fracture;
    scanning a laser along a visualization area of the test apparatus to enhance imaging of a distribution of the plurality of particles of the test fluid in the simulated fracture, wherein the visualization area includes the first flat surface portion and the second flat surface portion;
    generating data indicative of the distribution of the plurality of particles in the simulated fracture through the visualization area of the test apparatus subsequent to flowing the test fluid through the simulated fracture; and
    determining an adjustment for a size of the plurality of particles in the test fluid based on the data.

8. The method of claim 7, wherein positioning the first test component relative to the second test component comprises adjusting an actuator coupled to the second test component.

9. The method of claim 7, wherein flowing the test fluid through the simulated fracture comprises operating a pump of the test apparatus configured to displace the test fluid from the fluid vessel into a fluid inlet of the test apparatus.

10. The method of claim 7, wherein generating the data comprises capturing an image with a camera, capturing the image while scanning the visualization area with the laser, or scanning the visualization area with an ultrasonic device.

11. The method of claim 7, further comprising simulating downhole conditions by controlling a temperature, a pressure, or a combination thereof of the test apparatus.

12. The method of claim 7, wherein the simulated fracture comprises a tapered-width fracture with the first surface having a different angle than the second surface.

13. A test apparatus comprising:
    a conical cylinder comprising a first surface and a visualization area, the first surface comprising a conical inner surface and a first flat surface portion;
    a conical plug comprising a second surface including a conical outer surface and a second flat surface portion;
    an actuator coupleable to the conical plug, the actuator configured to position the conical plug relative to the conical cylinder to create a simulated fracture between the conical inner surface and the conical outer surface;
    the visualization area of the conical cylinder positionable along at least a portion of the simulated fracture, the visualization area including the first flat surface portion and the second flat surface portion;

a laser configured to be scanned along the visualization area to enhance imaging of a distribution of a plurality of particles of a test fluid flowing through the simulated fracture; and a fluid vessel defining an area containing the test fluid comprising the plurality of particles, a size of the plurality of particles being based on the distribution of the plurality of particles in the simulated fracture.

14. The test apparatus of claim 13, further comprising:

a fluid inlet configured to receive the test fluid at a first location of the test apparatus;

a fluid outlet configured to release at least a portion of the test fluid at a second location of the test apparatus; and a pump configured to displace the test fluid from the fluid vessel into the fluid inlet.

15. The test apparatus of claim 14, further comprising:

a camera configured to capture an image of the simulated fracture through the visualization area subsequent to the test fluid flowing from the fluid inlet to the fluid outlet.

16. The test apparatus of claim 14, wherein the simulated fracture comprises a tapered-width fracture with the conical inner surface having a different angle than the conical outer surface.

* * * * *